(12) United States Patent
Park et al.

(10) Patent No.: US 7,659,064 B2
(45) Date of Patent: Feb. 9, 2010

(54) PNA CHIP USING ZIP-CODES AND FABRICATION METHOD THEREOF

(75) Inventors: Hyun Gyu Park, Daejeon (KR); Jae Yang Song, Daejeon (KR)

(73) Assignee: Korea Advanced Institute of Sciences and Technology, Daejeon (KR)

( * ) Notice: Subject to any disclaimer, the term of this patent is extended or adjusted under 35 U.S.C. 154(b) by 610 days.

(21) Appl. No.: 11/113,534

(22) Filed: Apr. 25, 2005

(65) Prior Publication Data

US 2006/0115825 A1 Jun. 1, 2006

(30) Foreign Application Priority Data

Nov. 30, 2004 (KR) .................. 10-2004-0099514

(51) Int. Cl.
*C09J 163/00* (2006.01)
*C09J 4/00* (2006.01)
*C12Q 1/68* (2006.01)

(52) U.S. Cl. .................. 435/6; 977/792; 977/791; 156/330; 156/327

(58) Field of Classification Search .................. None
See application file for complete search history.

(56) References Cited

U.S. PATENT DOCUMENTS

| | | | | |
|---|---|---|---|---|
| 3,563,794 | A * | 2/1971 | Moriga | 427/381 |
| 2001/0039072 | A1 * | 11/2001 | Nagasawa et al. | 438/106 |
| 2006/0024703 | A1 * | 2/2006 | Zhang et al. | 435/6 |

FOREIGN PATENT DOCUMENTS

| | | | |
|---|---|---|---|
| JP | 2004-522175 | A1 | 7/2004 |
| KR | 1020030020232 | A1 | 8/2003 |
| WO | WO 0179548 | * | 10/2001 |
| WO | 03020978 | A1 | 3/2003 |

OTHER PUBLICATIONS

Arlinghaus et al., Analysis of Biosensor Chips for Identification of Nucleic Acids, 1997, Anal. Chem., vol. 69, pp. 3747-3753.*
Gerry, N.P. et al., *J. Mol. Biol.*, 292:251, 1999.
Hirschhorn, J.N., *Proc. Natl. Acad. Sci.*, 97:12164, 2000.
Nielsen, P.E. et al., *Sci.*, 254:1497, 1991.
Nielsen, P.E *Acc. Chem.Res.*, 32:624, 1999.
Dean, D.A., *Adv. Drug Delivery Rev.*, 44:81, 2000.

* cited by examiner

*Primary Examiner*—Marjorie Moran
*Assistant Examiner*—Jason M Sims
(74) *Attorney, Agent, or Firm*—Kelly K. Reynolds; Steven J. Hultquist; Intellectual Property/Technology Law

(57) ABSTRACT

A PNA zip-code chip in which PNA zip-code probes are immobilized on a substrate at high density using an epoxy compound as a linker, and method for fabricating such PNA chip. The use of PNA provides the chip with superior properties to DNA chips, allowing precise diagnosis of congenital diseases or base mutations with much higher sensitivity than is achievable with a DNA chip. The use of the PNA zip-code chip enables diagnosis of gene mutations in a simple manner, using only hybridization reaction, without the difficulties associated with processes in which probes must be immobilized directly on a substrate every time the target gene changes.

3 Claims, 6 Drawing Sheets

SEQUENCE LISTING

```
<160> NUMBER OF SEQ ID NOS: 55

<210> SEQ ID NO 1
<211> LENGTH: 12
<212> TYPE: DNA
<213> ORGANISM: Artificial Sequence
<220> FEATURE:
<223> OTHER INFORMATION: Synthetic Construct

<400> SEQUENCE: 1
tgcgggtaat cg                                                         12

<210> SEQ ID NO 2
<211> LENGTH: 12
<212> TYPE: DNA
<213> ORGANISM: Artificial Sequence
<220> FEATURE:
<223> OTHER INFORMATION: Synthetic Construct

<400> SEQUENCE: 2
tgcgacctat cg                                                         12

<210> SEQ ID NO 3
<211> LENGTH: 12
<212> TYPE: DNA
<213> ORGANISM: Artificial Sequence
```

-continued

```
<220> FEATURE:
<223> OTHER INFORMATION: Synthetic Construct

<400> SEQUENCE: 3
atcgtgcgac ct                                                        12

<210> SEQ ID NO 4
<211> LENGTH: 12
<212> TYPE: DNA
<213> ORGANISM: Artificial Sequence
<220> FEATURE:
<223> OTHER INFORMATION: Synthetic Construct

<400> SEQUENCE: 4
atcgggtatg cg                                                        12

<210> SEQ ID NO 5
<211> LENGTH: 12
<212> TYPE: DNA
<213> ORGANISM: Artificial Sequence
<220> FEATURE:
<223> OTHER INFORMATION: Synthetic Construct

<400> SEQUENCE: 5
cagcatcgtg cg                                                        12

<210> SEQ ID NO 6
<211> LENGTH: 12
<212> TYPE: DNA
<213> ORGANISM: Artificial Sequence
<220> FEATURE:
<223> OTHER INFORMATION: Synthetic Construct

<400> SEQUENCE: 6
cagcaccttg cg                                                        12

<210> SEQ ID NO 7
<211> LENGTH: 12
<212> TYPE: DNA
<213> ORGANISM: Artificial Sequence
<220> FEATURE:
<223> OTHER INFORMATION: Synthetic Construct

<400> SEQUENCE: 7
ggtaatcgac ct                                                        12

<210> SEQ ID NO 8
<211> LENGTH: 12
<212> TYPE: DNA
<213> ORGANISM: Artificial Sequence
<220> FEATURE:
<223> OTHER INFORMATION: Synthetic Construct

<400> SEQUENCE: 8
gaccatcgac ct                                                        12

<210> SEQ ID NO 9
<211> LENGTH: 12
<212> TYPE: DNA
<213> ORGANISM: Artificial Sequence
<220> FEATURE:
<223> OTHER INFORMATION: Synthetic Construct

<400> SEQUENCE: 9
gacccagcat cg                                                        12
```

<210> SEQ ID NO 10
<211> LENGTH: 12
<212> TYPE: DNA
<213> ORGANISM: Artificial Sequence
<220> FEATURE:
<223> OTHER INFORMATION: Synthetic Construct

<400> SEQUENCE: 10
acctgaccat cg                                                                 12

<210> SEQ ID NO 11
<211> LENGTH: 25
<212> TYPE: DNA
<213> ORGANISM: Artificial Sequence
<220> FEATURE:
<223> OTHER INFORMATION: Synthetic Construct

<400> SEQUENCE: 11
aagaagaagg tcgattacca aagga                                                   25

<210> SEQ ID NO 12
<211> LENGTH: 6232
<212> TYPE: DNA
<213> ORGANISM: Homo sapiens
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1530)..(1530)
<223> OTHER INFORMATION: n is a, c, g, or t
<220> FEATURE:
<221> NAME/KEY: misc_feature
<222> LOCATION: (2138)..(2138)
<223> OTHER INFORMATION: n is a, c, g, or t
<220> FEATURE:
<221> NAME/KEY: misc_feature
<222> LOCATION: (2961)..(2961)
<223> OTHER INFORMATION: n is a, c, g, or t
<220> FEATURE:
<221> NAME/KEY: misc_feature
<222> LOCATION: (3145)..(3145)
<223> OTHER INFORMATION: n is a, c, g, or t
<220> FEATURE:
<221> NAME/KEY: misc_feature
<222> LOCATION: (4296)..(4296)
<223> OTHER INFORMATION: n is a, c, g, or t

<400> SEQUENCE: 12
agccagcact gttcttggca catggtaatc ttaacatatt ttttcctaca gggaggcctg              60
gtgtcaggcc gggagtgggg tggaagggtc ccaaaatgga tggaagggcc ccaaaatggc            120
cgtgagcatc ctctgccctt gagaagagct agcccagctg tctagagctc cctgctgctg            180
ccgctctcgt aagcagcaag catttttggc tctcctgtct cagcatgatg cccctacaag            240
gttctttcgg gggtgggacc caacgctgct ctcctgatgg cctccctggc tcccagcacc            300
ttccatccca gctgctcagg gcccctcacc tgcgcctccc ccaccctccc ctctgcccac            360
tcccatcgca ggccatagct ccctgtccct ctccgctgcc atgaggcctg cactttgcag            420
ggctgaagtc caaagttcag tcccttcgct aagcacacgg ataaatatga accttggaga            480
atttccccag ctccaatgta aacagaacag gcagggccc  tgattcacgg gccgctgggg            540
ccagggttgg gggttggggg tgcccacagg gcttggctag tggggttttg gggggcagt             600 gggtgcaagg agtttggttt gtgtctgccg gccggcagga aaacgcaacc cacgcggtgg            660
gggaggcggc tagcgtggtg gacccgggcc gcgtggccct gtggcagccg agccatggtt            720

```
tctaaactga gccagctgca gacggagctc ctggcggccc tgctcgagtc agggctgagc    780
aaagaggcac tgatccaggc actgggtgag ccggggccct acctcctggc tggagaaggc    840
cccctggaca agggggagtc ctgcggcggc ggtcgagggg agctggctga gctgcccaat    900
gggctggggg agactcgggg ctccgaggac gagacggacg acgatgggga agacttcacg    960
ccacccatcc tcaaagagct ggagaacctc agccctgagg aggcggccca ccagaaagcc   1020
gtggtggaga cccttctgca gtaaggagcc ctgccccgtc cccgctccca ggagagccta   1080
gaggggcccc cctcagctcc taacgagccc cccttctgag ttgagtcccc atgaccttca   1140
gcctttagcc tagttgctgg aaggggggac agggcccatg agagcccagg ggtccttgct   1200
tggaggtttg agcctccagc ccctgaactg ctcctctgca gagtcccaaa tcccatgagc   1260
ccaggccttt agcccagtcc ttgggcnagg gggacatttc caggggggtc caagatggga   1320
gaaaaagcag tgaattcaca actcaaatgc ccacccaccc atccatccat ccgtccatcc   1380
acccattcat ccattcatcc attcacccat ccatccatcc acatatcttc atctgtgttg   1440
tgtgtctgtg tatccatgtt tctaaacctt tatctgttcc agtgtctgta tccataggcc   1500
tgtgtccacg tttgtcatgt gtgtgcgtcn acaagtctct gtcctcatga ccatgtgtct   1560
gtgtccctgt gtcctggcat aaatgaccat acctcaccgt ccctgagtct atgtgtaggc   1620
ccctgggctc cataactgct ttcatgcaca gtccccaccc tcagagttga caaggttcca   1680
gcacccagga ccgcagcccc acctatgggg agagacagcc cttgctgagc agatcccgtc   1740
cttgccctct cccagggagg acccgtggcg tgtggcgaag atggtcaagt cctacctgca   1800
gcagcacaac atcccacagc gggaggtggt cgataccact ggcctcaacc agtcccacct   1860
gtcccaacac ctcaacaagg gcactcccat gaagacgcag aagcgggccg ccctgtacac   1920
ctggtacgtc cgcaagcagc gagaggtggc gcagcgtaag taatgaccct accccgcatc   1980
ttccctggga gggcccagga ctctccccta actcataggt gggggctgga agcttcacca   2040
tccccattac acagacaggt agatggaaag gaagtcagtg ggattcaacc tgcatttatt   2100
acctattctg cgccaggcac tctgtgggac gggagtanac ttggtcctga acatccaaag   2160
atgaatgaaa tgggtccctg ctttctttt cttttttag atacgtgact ctggaaaaat    2220
atgtaagctc tctgagcctc agcttcttca tctgtacaat ggggatagta aatgtgccaa   2280
atcagaacaa atgctaatgc ttacctgcag tcttgtactg agaaggatgg tgagatcata   2340 tcttggttg gtaggaaagc attcagggat tgattagtga tgtttgcctt gaacacaggt    2400
taagaaagtg atggcatgtg tgctgtgtgt ttgtcatcag tagattagat gatttctaag   2460
ttctagctgt aagctcctct ggttcagcgc catggcaatg agaaagaatc aagggcaagg   2520 tcagggaat ggacgaggga aggtgagagt ggccagtacc ccactcacgg ctttctgtgc    2580
ctgcagagtt cacccatgca gggcaggag ggctgattga agagcccaca ggtgatgagc    2640
taccaaccaa gaaggggcgg aggaaccgtt tcaagtgggg cccagcatcc cagcagatcc   2700
tgttccaggc ctatgagagg cagaagaacc ctagcaagga ggagcgagag acgctagtgg   2760
aggagtgcaa taggtacaac ggcgggcggg aaacagtgct ggtttggtct gggctgcggc   2820
aaggccaggg gaaggggaag gtgactctag gtcctgtaaa aggctgtcca gttgccgaga   2880
actcctgata ttggcttagc ctggcccaga aaattgagaa tacttgaacc taagcccatt   2940
cctcgcagcc cccctgcacc ntggacacca agcaacccct tccatggatg ctcacccaat   3000
tcgattctct ctacaatcct atggctcttt tgctcacttt atgaatggag agactgaggt   3060
```

```
cagacagact gtcaattgcc caaggtcaca cagcagacct ggcattggaa cccagatctg    3120
ccagcctcaa accctccggc agagntcagc ttctcagaac cctccccttc atgcccagga    3180
cagggttcct ctgagcctgg cctggaggct catgggtggc tatttctgca gggcggaatg    3240
catccagaga ggggtgtccc catcacaggc acagggctg ggctccaacc tcgtcacgga     3300
ggtgcgtgtc tacaactggt ttgccaaccg gcgcaaagaa gaagccttcc ggcacaagct    3360
ggccatggac acgtacagcg gccccccccc agggccaggc ccgggacctg cgctgcccgc    3420
tcacagctcc cctggcctgc ctccacctgc cctctccccc agtaaggtcc acggtaagtg    3480
gtatgtgggg acaagggaca cgtgggaagg tgggagggtt gggaggact gtcccattga     3540 cagcagtcac ctaaacctct ttgcacgtca gtttggttcc attcgcagct gacccaggga    3600
ttggcaaaag gtagaaacaa aggcagattt gctggctgca taaaggcaga caggcagatg    3660
gcctaagcaa accaatggag tttgaagtgc tgagggctgt ggaggcaggg gagggcaggg    3720
aagtggggtg ctgaggcagg acactgcttc cctctccagg tgtgcgctat ggacagcctg    3780
cgaccagtga gactgcagaa gtaccctcaa gcagcggcgg tcccttagtg acagtgtcta    3840
cacccctcca ccaagtgtcc cccacgggcc tggagcccag ccacagcctg ctgagtacag    3900
aagccaagct ggtgagtgtc cttgcttgta aggaaaaccc aacctcatct ttccttggca    3960
gggagattct ggagcagtcc ctagggaggc cctgtgggga ccccggcccc ccggacacag    4020
cttggcttcc cctcgtaggt ctcagcagct gggggccccc tcccccctgt cagcaccctg    4080
acagcactgc acagcttgga gcagacatcc ccaggcctca accagcagcc cagaacctc     4140 atcatggcct cacttcctgg ggtcatgacc atcgggcctg gtgagcctgc ctccctgggt    4200
cctacgttca ccaacacagg tgcctccacc ctggtcatcg gtaagctggt ggggatgggt    4260
gggcacctgg gtgggaggct catggggcaa ccgcanaatc caggagctgg aaaagccact    4320
gggactcatt cattcattca ttcattcata caacatgtta ggagagggga gcagagaact    4380
gaccccatgg cctttgcact gctgtggtac cccagggctc cagggaaccg cagtttgaca    4440
acttttgaac aagtcaccgc ttgctttttcc cattagctta gacaaagagc taaaggctca    4500
gagaggggga atgacttgcc agagccactt aaattagtgg caggtcccag tggagggctg    4560
tttcctgacc accttgcccc ttcttccaaa ccacgggctc tgggaaggag aggtggtgcc    4620
cttgggaggt cttgggcagg ggtgggatat aactgggggg cccagctgat tccctcccct    4680
tccactccag gcctggcctc cacgcaggca cagagtgtgc cggtcatcaa cagcatgggc    4740
agcagcctga ccaccctgca gcccgtccag ttctcccagc cgctgcaccc ctcctaccag    4800
cagccgctca tgccacctgt gcagagccat gtgacccaga accccttcat ggccaccatg    4860
gctcagctgc agagccccca cggtgagcac cctgtgcccc acacagcagg agatgatgat    4920
agaggttggc tgtcaatgga tgcagggaa aggggtgcct ggcaggcatt gcagtctgca     4980
tgtgtctctg gacaagtgt gttccgtga ttgagggtgt ctgcaggcca gtgtgttccc      5040
atgtgaatgc acgtatctgt gtgtgtgcac gactgcttgt gtgagcagat ccctagtgcg    5100
tgtctgggtg tgtatcggtt gtgcatgcat ttgtgtgcat gcctgtgttt ctctgaaact    5160
cttagggcca tatgaatttc taaaatctat tcagaccagt tttgaaaatc agccttggat    5220
ctccaactgc tgcccagtct ggctgttcag caggcccat gccccctttt ccccagtctt     5280
gaggcctggg actagggctg tcaggcacgt ttgccacgtc tgcccctctc tccctgcgg     5340 ccagccctct acagccacaa gcccgaggtg gcccagtaca cccacacggg cctgctcccg    5400
cagactatgc tcatcaccga caccaccaac ctgagcgccc tggccagcct cacgcccacc    5460
```

```
aagcaggtaa ggtccaggcc tgctggccct ccctcggcct gtgacagagc ccctcacccc     5520
cacatccccc gggctcagga ggctgctctg ctcccccagg tcttcacctc agacactgag     5580
gcctccagtg agtccgggct tcacacgccg gcatctcagg ccaccaccct ccacgtcccc     5640
agccaggacc ctgccggcat ccagcacctg cagccggccc accggctcag cgccagcccc     5700
acaggtgaga ggccctggct ccaccccctc ccttactgtc cctgcccct tccatgttgg      5760 tcccacccct tctgttgctg tccgtcactg tggggctgtg catgcagcag gcctagggct     5820
gctgtgagga agcactggca ggcgtggaag ggtggggtgg cttccatgaa tccagtgttc     5880
acagtaagat gtactcaggc cagtccatgg gcggccgtgg accctggctg ggaggctccc     5940
tttgttaaga accagggta gaggtgtgac tttggggttc ctgttatgtg ctgtgatcca      6000
ggaggtgtgg ccctgcctcc ccatcctgag taccctagg gacaggcagg tggggtgggt     6060
gtgggtgcct ggtgggtggc tagcagcctt gtttgcctct gcagtgtcct ccagcagcct    6120
ggtgctgtac cagagctcag actccagcaa tggccagagc cacctgctgc catccaacca    6180
cagcgtcatc gagaccttca tctccaccca gatggcctct tcctcccagt aa            6232
```

```
<210> SEQ ID NO 13
<211> LENGTH: 33
<212> TYPE: DNA
<213> ORGANISM: Artificial Sequence
<220> FEATURE:
<223> OTHER INFORMATION: Synthetic Construct

<400> SEQUENCE: 13
taccaggtcg cagataccac tggcctcaac cag                                  33

<210> SEQ ID NO 14
<211> LENGTH: 31
<212> TYPE: DNA
<213> ORGANISM: Artificial Sequence
<220> FEATURE:
<223> OTHER INFORMATION: Synthetic Construct

<400> SEQUENCE: 14
cgcaaggtgc tgcactggcc tcaaccagtc c                                    31

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
tgctgggtca gatggtcaag t                                               21

<210> SEQ ID NO 16
<211> LENGTH: 12
<212> TYPE: DNA
<213> ORGANISM: Artificial Sequence
<220> FEATURE:
<223> OTHER INFORMATION: Synthetic Construct

<400> SEQUENCE: 16
tgcgggtaca gc                                                         12

<210> SEQ ID NO 17
<211> LENGTH: 12
<212> TYPE: DNA
```

```
<213> ORGANISM: Artificial Sequence
<220> FEATURE:
<223> OTHER INFORMATION: Synthetic Construct

<400> SEQUENCE: 17
tgcggaccat cg                                                              12

<210> SEQ ID NO 18
<211> LENGTH: 12
<212> TYPE: DNA
<213> ORGANISM: Artificial Sequence
<220> FEATURE:
<223> OTHER INFORMATION: Synthetic Construct

<400> SEQUENCE: 18
tgcggaccac ct                                                              12

<210> SEQ ID NO 19
<211> LENGTH: 12
<212> TYPE: DNA
<213> ORGANISM: Artificial Sequence
<220> FEATURE:
<223> OTHER INFORMATION: Synthetic Construct

<400> SEQUENCE: 19
tgcgacctgg ta                                                              12

<210> SEQ ID NO 20
<211> LENGTH: 12
<212> TYPE: DNA
<213> ORGANISM: Artificial Sequence
<220> FEATURE:
<223> OTHER INFORMATION: Synthetic Construct

<400> SEQUENCE: 20
atcgggtaga cc                                                              12

<210> SEQ ID NO 21
<211> LENGTH: 12
<212> TYPE: DNA
<213> ORGANISM: Artificial Sequence
<220> FEATURE:
<223> OTHER INFORMATION: Synthetic Construct

<400> SEQUENCE: 21
atcggacctg cg                                                              12

<210> SEQ ID NO 22
<211> LENGTH: 12
<212> TYPE: DNA
<213> ORGANISM: Artificial Sequence
<220> FEATURE:
<223> OTHER INFORMATION: Synthetic Construct

<400> SEQUENCE: 22
atcgaccttg cg                                                              12

<210> SEQ ID NO 23
<211> LENGTH: 12
<212> TYPE: DNA
<213> ORGANISM: Artificial Sequence
<220> FEATURE:
<223> OTHER INFORMATION: Synthetic Construct

<400> SEQUENCE: 23
atcgacctca gc                                                              12
```

```
<210> SEQ ID NO 24
<211> LENGTH: 12
<212> TYPE: DNA
<213> ORGANISM: Artificial Sequence
<220> FEATURE:
<223> OTHER INFORMATION: Synthetic Construct

<400> SEQUENCE: 24
cagcatcgac ct                                                              12

<210> SEQ ID NO 25
<211> LENGTH: 12
<212> TYPE: DNA
<213> ORGANISM: Artificial Sequence
<220> FEATURE:
<223> OTHER INFORMATION: Synthetic Construct

<400> SEQUENCE: 25
cagcggtaat cg                                                              12

<210> SEQ ID NO 26
<211> LENGTH: 12
<212> TYPE: DNA
<213> ORGANISM: Artificial Sequence
<220> FEATURE:
<223> OTHER INFORMATION: Synthetic Construct

<400> SEQUENCE: 26
cagcggtaga cc                                                              12

<210> SEQ ID NO 27
<211> LENGTH: 12
<212> TYPE: DNA
<213> ORGANISM: Artificial Sequence
<220> FEATURE:
<223> OTHER INFORMATION: Synthetic Construct

<400> SEQUENCE: 27
cagcgacctg cg                                                              12

<210> SEQ ID NO 28
<211> LENGTH: 12
<212> TYPE: DNA
<213> ORGANISM: Artificial Sequence
<220> FEATURE:
<223> OTHER INFORMATION: Synthetic Construct

<400> SEQUENCE: 28
cagcacctga cc                                                              12

<210> SEQ ID NO 29
<211> LENGTH: 12
<212> TYPE: DNA
<213> ORGANISM: Artificial Sequence
<220> FEATURE:
<223> OTHER INFORMATION: Synthetic Construct

<400> SEQUENCE: 29
ggtatgcgga cc                                                              12

<210> SEQ ID NO 30
<211> LENGTH: 12
<212> TYPE: DNA
<213> ORGANISM: Artificial Sequence
<220> FEATURE:
```

<223> OTHER INFORMATION: Synthetic Construct

<400> SEQUENCE: 30
ggtaatcgtg cg                                                          12

<210> SEQ ID NO 31
<211> LENGTH: 12
<212> TYPE: DNA
<213> ORGANISM: Artificial Sequence
<220> FEATURE:
<223> OTHER INFORMATION: Synthetic Construct

<400> SEQUENCE: 31
ggtacagcat cg                                                          12

<210> SEQ ID NO 32
<211> LENGTH: 12
<212> TYPE: DNA
<213> ORGANISM: Artificial Sequence
<220> FEATURE:
<223> OTHER INFORMATION: Synthetic Construct

<400> SEQUENCE: 32
ggtacagcga cc                                                          12

<210> SEQ ID NO 33
<211> LENGTH: 12
<212> TYPE: DNA
<213> ORGANISM: Artificial Sequence
<220> FEATURE:
<223> OTHER INFORMATION: Synthetic Construct

<400> SEQUENCE: 33
ggtagacctg cg                                                          12

<210> SEQ ID NO 34
<211> LENGTH: 12
<212> TYPE: DNA
<213> ORGANISM: Artificial Sequence
<220> FEATURE:
<223> OTHER INFORMATION: Synthetic Construct

<400> SEQUENCE: 34
ggtagaccac ct                                                          12

<210> SEQ ID NO 35
<211> LENGTH: 12
<212> TYPE: DNA
<213> ORGANISM: Artificial Sequence
<220> FEATURE:
<223> OTHER INFORMATION: Synthetic Construct

<400> SEQUENCE: 35
ggtaaccttg cg                                                          12

<210> SEQ ID NO 36
<211> LENGTH: 12
<212> TYPE: DNA
<213> ORGANISM: Artificial Sequence
<220> FEATURE:
<223> OTHER INFORMATION: Synthetic Construct

<400> SEQUENCE: 36
ggtaacctca gc                                                          12

<210> SEQ ID NO 37
<211> LENGTH: 12
<212> TYPE: DNA
<213> ORGANISM: Artificial Sequence
<220> FEATURE:
<223> OTHER INFORMATION: Synthetic Construct

<400> SEQUENCE: 37
gactatcgtg cg                                                    12

<210> SEQ ID NO 38
<211> LENGTH: 12
<212> TYPE: DNA
<213> ORGANISM: Artificial Sequence
<220> FEATURE:
<223> OTHER INFORMATION: Synthetic Construct

<400> SEQUENCE: 38
gacccagcac ct                                                    12

<210> SEQ ID NO 39
<211> LENGTH: 12
<212> TYPE: DNA
<213> ORGANISM: Artificial Sequence
<220> FEATURE:
<223> OTHER INFORMATION: Synthetic Construct

<400> SEQUENCE: 39
gaccaccttg cg                                                    12

<210> SEQ ID NO 40
<211> LENGTH: 12
<212> TYPE: DNA
<213> ORGANISM: Artificial Sequence
<220> FEATURE:
<223> OTHER INFORMATION: Synthetic Construct

<400> SEQUENCE: 40
gaccacctat cg                                                    12

<210> SEQ ID NO 41
<211> LENGTH: 12
<212> TYPE: DNA
<213> ORGANISM: Artificial Sequence
<220> FEATURE:
<223> OTHER INFORMATION: Synthetic Construct

<400> SEQUENCE: 41
acctatcgtg cg                                                    12

<210> SEQ ID NO 42
<211> LENGTH: 12
<212> TYPE: DNA
<213> ORGANISM: Artificial Sequence
<220> FEATURE:
<223> OTHER INFORMATION: Synthetic Construct

<400> SEQUENCE: 42
acctatcgca gc                                                    12

<210> SEQ ID NO 43
<211> LENGTH: 12
<212> TYPE: DNA
<213> ORGANISM: Artificial Sequence
<220> FEATURE:
<223> OTHER INFORMATION: Synthetic Construct

```
<400> SEQUENCE: 43
acctcagcga cc                                                              12

<210> SEQ ID NO 44
<211> LENGTH: 12
<212> TYPE: DNA
<213> ORGANISM: Artificial Sequence
<220> FEATURE:
<223> OTHER INFORMATION: Synthetic Construct

<400> SEQUENCE: 44
acctggtaat cg                                                              12

<210> SEQ ID NO 45
<211> LENGTH: 12
<212> TYPE: DNA
<213> ORGANISM: Artificial Sequence
<220> FEATURE:
<223> OTHER INFORMATION: Synthetic Construct

<400> SEQUENCE: 45
acctgacctg cg                                                              12

<210> SEQ ID NO 46
<211> LENGTH: 32
<212> TYPE: DNA
<213> ORGANISM: Artificial Sequence
<220> FEATURE:
<223> OTHER INFORMATION: Synthetic Construct

<400> SEQUENCE: 46
cgattacccg cagcagcaca acatcccaca gc                                        32

<210> SEQ ID NO 47
<211> LENGTH: 33
<212> TYPE: DNA
<213> ORGANISM: Artificial Sequence
<220> FEATURE:
<223> OTHER INFORMATION: Synthetic Construct

<400> SEQUENCE: 47
cgataggtcg catacctgca gcagcacaac atc                                       33

<210> SEQ ID NO 48
<211> LENGTH: 27
<212> TYPE: DNA
<213> ORGANISM: Artificial Sequence
<220> FEATURE:
<223> OTHER INFORMATION: Synthetic Construct

<400> SEQUENCE: 48
aggtcgcacg atccgtggcg tgtggcg                                              27

<210> SEQ ID NO 49
<211> LENGTH: 32
<212> TYPE: DNA
<213> ORGANISM: Artificial Sequence
<220> FEATURE:
<223> OTHER INFORMATION: Synthetic Construct

<400> SEQUENCE: 49
cgcatacccg atagcagcac aacatcccac ag                                        32

<210> SEQ ID NO 50
<211> LENGTH: 29
```

```
<212> TYPE: DNA
<213> ORGANISM: Artificial Sequence
<220> FEATURE:
<223> OTHER INFORMATION: Synthetic Construct

<400> SEQUENCE: 50
cgcacgatgc tgacagcggg aggtggtcg                                       29

<210> SEQ ID NO 51
<211> LENGTH: 31
<212> TYPE: DNA
<213> ORGANISM: Artificial Sequence
<220> FEATURE:
<223> OTHER INFORMATION: Synthetic Construct

<400> SEQUENCE: 51
cgcaaggtgc tgcactggcc tcaaccagtc c                                    31

<210> SEQ ID NO 52
<211> LENGTH: 28
<212> TYPE: DNA
<213> ORGANISM: Artificial Sequence
<220> FEATURE:
<223> OTHER INFORMATION: Synthetic Construct

<400> SEQUENCE: 52
aggtcgatta ccgacgcaga agcgggcc                                        28

<210> SEQ ID NO 53
<211> LENGTH: 34
<212> TYPE: DNA
<213> ORGANISM: Artificial Sequence
<220> FEATURE:
<223> OTHER INFORMATION: Synthetic Construct

<400> SEQUENCE: 53
aggtcgatgg tcaaccagtc ccacctgtcc caac                                 34

<210> SEQ ID NO 54
<211> LENGTH: 32
<212> TYPE: DNA
<213> ORGANISM: Artificial Sequence
<220> FEATURE:
<223> OTHER INFORMATION: Synthetic Construct

<400> SEQUENCE: 54
cgatgctggg tctcccatga agacgcagaa gc                                   32

<210> SEQ ID NO 55
<211> LENGTH: 33
<212> TYPE: DNA
<213> ORGANISM: Artificial Sequence
<220> FEATURE:
<223> OTHER INFORMATION: Synthetic Construct

<400> SEQUENCE: 55
cgatggtcag gtcctacctg cagcagcaca aca                                  33
```

PNA CHIP USING ZIP-CODES AND FABRICATION METHOD THEREOF

CROSS-REFERENCE TO RELATED APPLICATION

This application claims priority under 35 USC 119 of Korean Patent Application No. 10-2004-0099514 filed Nov. 30,2004.

BACKGROUND OF THE INVENTION

1. Field of the Invention

The present invention relates to a PNA chip using zip-codes and to a method for fabricating the same. More particularly, the invention relates to a PNA zip-code chip in which PNA zip-code probes are immobilized at high density using an epoxy compound as a linker, as well as to a method for fabricating the same.

2. Background of the Related Art

As large amounts of genetic information are developed as a result of genome projects involving various organisms, including human genome projects, studies to interpret such genetic information and to analyze the relation thereof are actively being conducted. The focus of studies in the fields of molecular biology and bioengineering is changing from the structural interpretation of DNA to the functional interpretation of genes and the identification of the relation between genes. As a result of this change, various methods for analyzing genetic information are now developed. In particular, DNA chips are attracting attention as a means of analyzing a sample more effectively using the huge amounts of genetic information resulting from genome projects, since such chips can analyze such huge amounts of genetic information in a short time, and their use is easily automated.

A DNA chip is a chip in which 1,000-1,000,000 oligonucleotides, each containing 8-25 bases, are arranged and attached on a solid surface, such as silicon, surface-modified glass, polypropylene or activated polyacrylamide. DNA to be immobilized on the chip is determined depending on the DNA base sequence of a target gene. This DNA chip has various applications comparable to recombinant gene technology and polymerase chain reaction (PCR), and also possesses advantages surpassing the prior technology. The DNA chip can be applied to a wide range of subjects, depending on the way it is used, and thus has a wide range of application fields. The use of the DNA chip makes it possible to analyze even a very small amount of a sample and to identify the base sequences of a target gene at various sites at the same time.

A DNA analysis system utilizing the DNA chip is expected to quicken the speed of DNA analysis by tens to hundreds of times, thus greatly shortening the completion time of the genome projects of various organisms that are currently being conducted and greatly lowering the current unit cost of analysis per base. Such DNA analysis system is applicable to a wide range of fields, including the diagnosis of congenital diseases, the investigation of mutations, cancer diagnosis, the detection of pathogenic bacteria, the analysis of gene expression, and the development of new drugs.

A DNA chip with zip-codes (Gerry, N. P. et al., *J. Mol. Biol.*, 292:251, 1999; Hirschhorn, J. N., *Proc. Natl. Acad. Sci.*, 97:12164, 2000) is fabricated by immobilizing probes with a given length of base sequences having no homology with each other on a solid substrate and designing the base sequence of a target DNA to be hybridized on the chip in such a manner that the 5'-terminal end of the target gene has a base sequence complementary to the probes and the 3'-terminal end has a base sequence complementary to the gene. Thus, the DNA chip has advantages, in that it can be fabricated in a simple manner and it can obtain diagnostic results on the same chip by reconstructing the base sequence site of a target DNA to match with a gene without a separate process for constructing probes.

PNA, an analog of DNA, has a peptide bond as a flame and contains four kinds of bases as in DNA. Unlike DNA, PNA bears no negative charge at the frame (Nielsen, P. E. et al., *Sci.*, 254:1497, 1991). FIG. 1 shows the structure of DNA having a sugar-phosphate flame and the structure of PNA having a peptide bond frame. PNA has a higher stability than DNA against nuclease and various chemicals, and is more stable than DNA in a wide range of temperature and pH. PNA forms strong bonds with DNA and RNA and has a higher specificity and selectivity than DNA (Nielsen, P. E *Acc. Chem.Res.*, 32:624, 1999). As a result, PNA is useful in many applications, including antigen-antibody reaction, hybridization technology and drug delivery (Dean, D. A., *Adv. Drug Delivery Rev.*, 44:81,2000).

DNA chips developed to date are fabricated by cumbersome processes in which the base sequences of probes immobilized on the chip match with the target DNA, depending on the kinds of base mutations or SNPs to be diagnosed. In other words, probes constituting the DNA chip must be reconstructed depending on the type of target DNA to be diagnosed, which is troublesome and increases the fabrication cost of the chip.

SUMMARY OF THE INVENTION

The present inventors have made extensive efforts to solve the above-described problems, and consequently found that the use of a PNA chip fabricated by a zip-code technique using PNA having superior properties to DNA, allows precise analysis of multiple bases, base mutations and SNPs with high sensitivity, thereby perfecting the present invention.

The present invention relates to a method for fabricating a PNA zip-code chip by immobilizing PNA probes on an antinated substrate (a substrate modified with amine) using an epoxy compound as a linker.

The present invention also relates to a PNA zip-code chip in which PNA zip-code probes are immobilized on a substrate using an epoxy compound as a linker.

The present invention also relates to methods for detecting DNA and analyzing multiple base mutations and single nucleotide polymorphisms (SNPs), which comprise using the PNA chip.

Other aspects, features and advantages of the invention will be more fully apparent from the ensuing disclosure and appended claims.

BRIEF DESCRIPTION OF THE DRAWINGS

FIG. 5(A) shows the ability of single nucleotide polymorphism detection of the PNA zip-code chip according to changes in the concentration of hybridization solution, and FIG. 5(B) shows the ability of single nucleotide polymorphism detection of the DNA zip-code chip according to changes in the concentration of hybridization solution.

FIG. 7(A) is a schematic representation of the arrangement of PNA zip-code chips (numerals represent the positions of genes, and AA, GG, CC and TT represent the normal phenotypes of the genes), and FIG. 7(B) shows fluorescent images illustrating the results of simultaneous detection of 10 base mutations in four PNA chips.

DETAILED DESCRIPTION OF THE INVENTION AND PREFERRED EMBODIMENT THEREOF

Figure 1:
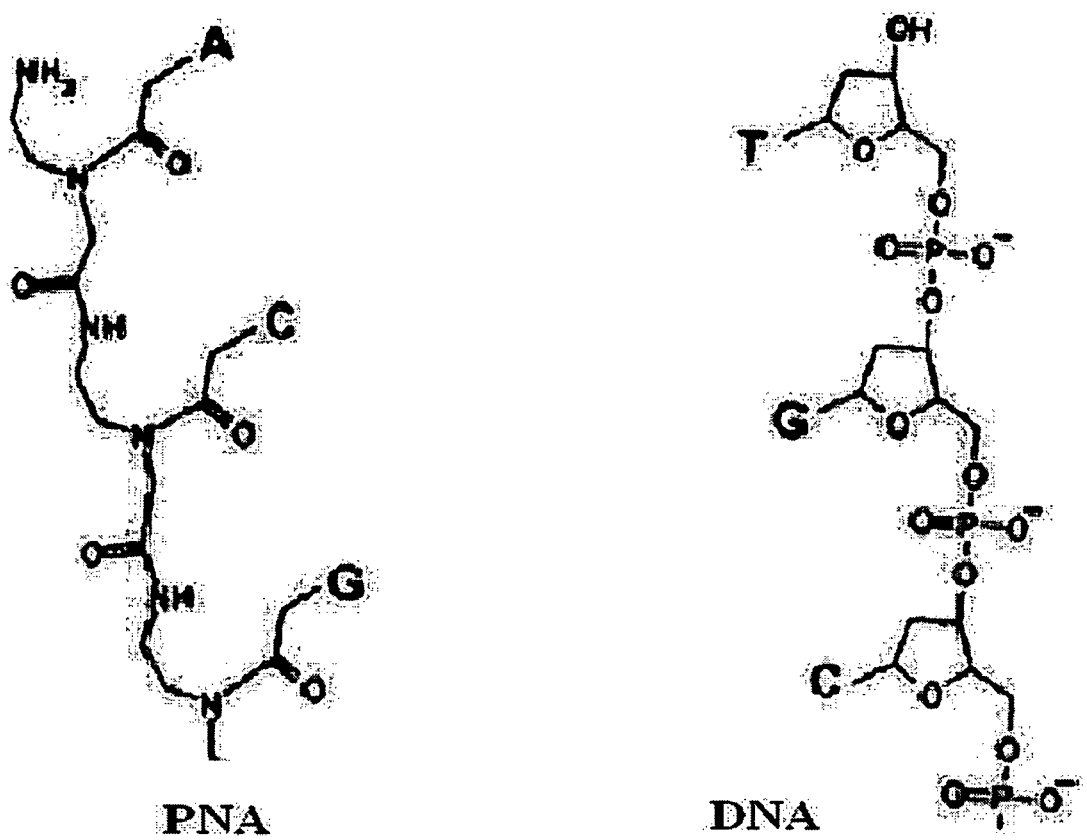
FIG. 1 shows the structural formulas of PNA (peptide nucleic acid) and DNA.

In one aspect, the present invention provides a method for fabricating a PNA chip using zip-codes, the method comprising the steps of: (a) spotting a mixture of dimethylsulfoxide (DMSO), a PNA zip-code probe and an epoxy compound on an aminated substrate so as to immobilize the PNA probe on the substrate; and (b) washing the PNA zip-code probe-immobilized substrate with an SDS solution, followed by drying.

In the inventive method, the volume ratio of the dimethylsulfoxide (DMSO), the PNA probe and the epoxy compound in step (a) is preferably 1:1:1, and the epoxy compound is preferably represented by the following formula 1:

[Formula 1]

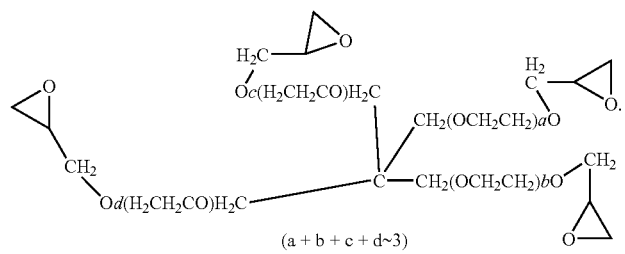

In the inventive method, the concentration of the PNA zip-code probe is preferably 10 µM to 1 mM. Also, the PNA zip-code probes are preferably plural and such plural PNA zip-code probes contain base sequences having a homology of less than 30% with each other. The PNA zip-code probe preferably contains any one of SEQ ID NO: 1 to SEQ ID NO: 10. In a further aspect, the PNA zip-code probe contains any one of SEQ ID NO: 1 to SEQ ID NO: 10 and SEQ ID NO: 16 to SEQ ID NO: 45.

In another aspect, the present invention provides a PNA zip-code chip fabricated by the foregoing method, in which the PNA zip-code probe is immobilized using an epoxy compound as a linker.

In yet another aspect, the present invention provides a method for detecting a target DNA, the method comprising the step of hybridizing the target DNA with the PNA zip-code chip. In this method, the detection is performed using a fluorescent signal.

In still another aspect, the present invention provides a method for analyzing multiple base mutations, such method including and the steps of: (a) selecting the base mutation sites of a target gene; (b) designing a single base extension (SBE) primer; (c) amplifying the target gene of the step (a) by polymerase chain reaction (PCR); (d) subjecting the amplified target gene to SBE reaction using the SBE primer of the step (b) and ddATP, ddTTP, ddCTP or ddGTP labeled with a fluorescent substance; (e) hybridizing the SBE reaction product with the PNA zip-code chip; and (f) detecting the signal of the fluorescent substance.

In this inventive method, the SBE primer preferably contains a sequence complementary to the PNA zip-code immobilized on the PNA zip-code chip at the 5'-terminal end and a sequence complementary to the target gene at the 3' terminal end. Also, the SBE primers are plural. Furthermore, the target gene is preferably diabetes-associated gene HNF 1-α.

In another further aspect, the present invention provides a method for analyzing multiple base mutations, the method comprising the steps of: (a) selecting the base mutation sites of a target gene; (b) designing an SBE primer; (c) amplifying the target gene of step (a) by PCR; (d) subjecting the amplified target gene to SBE reactions in four tubes which contain dATP, ddTTP, ddCTP and ddGTP, respectively using the SBE primer of step (b) and a ddNTP labeled with a specific compound; (e) hybridizing the SBE reaction product with the PNA zip-code chip; and (f) detecting the signal of the labeled compound.

In this method, the SBE primer preferably contains a sequence complementary to the PNA zip-code immobilized on the PNA zip code chip at the 5'-terminal end and a sequence complementary to the target gene at the 3'-terminal end. Also, the SBE primers are preferably plural.

Also in this inventive method, the specific compound preferably is biotin. The step of detecting the signal is performed by staining with phycoerytlrin conjugated with streptavidin, which is a protein having strong affinity with biotin.

In still another aspect, the present invention provides a method for analyzing SNPs, wherein the method is characterized by using the PNA chip.

The present invention is described in greater detail hereinafter.

The zip-code chip is a chip wherein probes (zip-codes) containing a given length of base sequences having no homology with each other are immobilized on a solid substrate. Specifically, the zip-code chip refers to a chip in which an oligonucleotide having a sequence homologous with the base sequence of the probe at the 5' terminal end and a sequence complementary to the base sequence of a target DNA at the 3' terminal end is hybridized with the chip to detect a signal.

In the present invention, base sequences having the lowest homology with each other are selected for use in the probe, and the probe having such base sequences refers to a zip-code.

In the present invention, PNA is used as the probe of the zipcode chip.

Any target substances may be used for hybridization in the present invention without limitation if they are detectible by reaction or linking with the PNA probe. Preferred examples of such target substances include living body-derived molecules, such as DNA, RNA and the like.

In the present invention, the PNA zip-code probe is immobilized on an aminated solid substrate, and this immobilization is performed by chemically linking PNA to the aminated solid substrate using an epoxy compound as a linker.

The substrate itself may be formed of any suitable material of a construction, e.g., silicon, glass, surface-modified glass, polypropylene, activated polyacrylamide, etc. The substrate may be animated in any suitable manner, utilizing any of various animation agents that are commercially available, the choice of a specific animation agent being within the skill of the art, for a particular substrate, based on the disclosure herein.

The epoxy compound used in the present invention, in one preferred embodiment, has a structure represented by formula 1 below.

Figure 2:
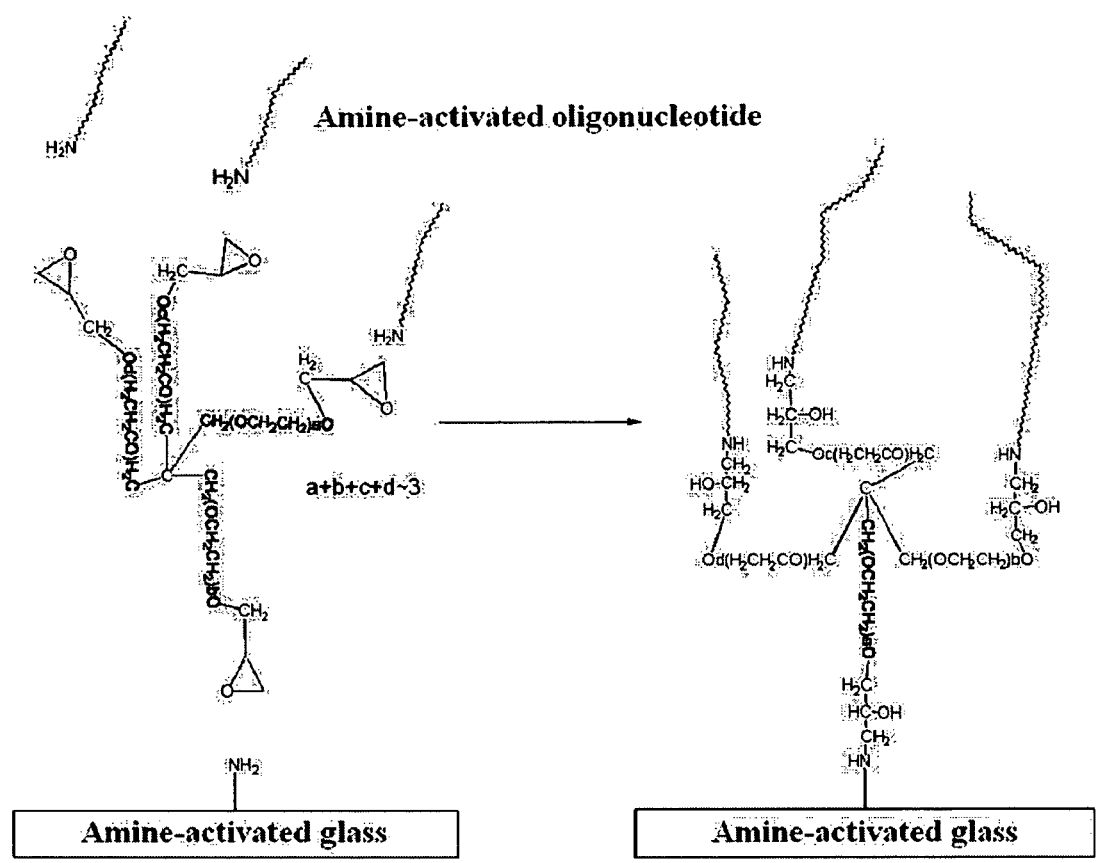
FIG. 2 schematically depicts the inventive method for immobilizing DNA, PNA and the like on an aminated glass substrate using an epoxy compound.

As shown in FIG. 2, the epoxy group of the epoxy compound binds chemically to the aminated glass substrate, and the amine group of the PNA probe binds chemically to other epoxy group of the epoxy compound linked to the glass substrate.

In this way, the PNA probe is immobilized on the glass substrate, and some linkages caused by the physical adsorption between the PNA zipcode probe and the glass substrate also occur.

of SEQ ID NO: 1 to SEQ ID NO: 10, respectively, which have low sequence homology with each other. Each of the base sequences has 12 bases. Since the N-terminal end of the PNA probes has an amine (—$NH_2$) group, the linkage between the amine group and the epoxy group was used to immobilize the probe on the substrate.

```
N-TGCGGGTAATCG-C    (SEQ ID NO: 1)

N-TGCGACCTATCG-C    (SEQ ID NO: 2)

N-ATCGTGCGACCT-C    (SEQ ID NO: 3)

N-ATCGGGTATGCG-C    (SEQ ID NO: 4)

N-CAGCATCGTGCG-C    (SEQ ID NO: 5)

N-CAGCACCTTGCG-C    (SEQ ID NO: 6)

N-GGTAATCGACCT-C    (SEQ ID NO: 7)

N-GACCATCGACCT-C    (SEQ ID NO: 8)

N-GACCCAGCATCG-C    (SEQ ID NO: 9)

N-ACCTGACCATCG-C    (SEQ ID NO: 10)
```

The PNA zip-code probes were immobilized on the glass substrate in the following manner, thus fabricating a PNA zip-code chip.

Dimethylsulfoxide (DMSO), the PNA zip-code probe and the epoxy compound were mixed with each other at a volume ratio of 1:1:1 to obtain a mixture containing PNA at a final concentration of 100 µM. The mixture was spotted on an aminated glass substrate by means of a spotter. Thereafter, the

[Formula 1]

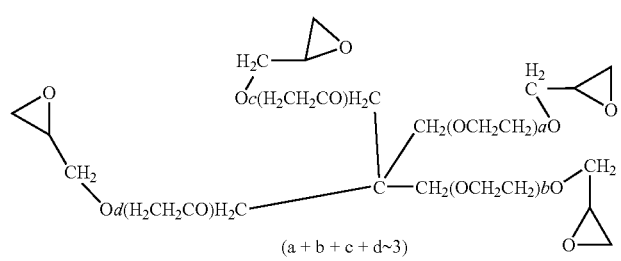

(a + b + c + d~3)

EXAMPLES

The present invention will hereinafter be described in further detail by examples. It will however be obvious to a person skilled in the art that these examples can be modified into various different forms and that the present invention is not limited to or by the examples. These examples are presented to further illustrate the present invention.

Example 1

Fabrication of PNA Zip-Code Chip

In this Example, an aminated glass substrate was used as a substrate of a PNA chip. 10 PNA zip-code probes were immobilized on the substrate. These probes contain base sequences spotted substrate was washed with 0.2% SDS solution and dried at room temperature, thus fabricating a PNA zip-code chip.

Example 2

Hybridization of DNA with PNA Zip-Code Chip

In order to test the hybridization ability of the PNA zip-code chip with DNA, a hybridization test was performed using a PNA zip-code chip fabricated according to the method of Example 1, in which four PNA zip-code probes having the base sequences of SEQ ID NO: 3, SEQ ID NO: 6, SEQ ID NO: 7 and SEQ ID NO: 9 were immobilized.

First, a target DNA (SEQ ID NO: 11) having 25 bases labeled with a fluorescent substance (Cy3) was prepared. 30 µl of hybridization solution, 6× SSPET (saline sodium phosphate EDTA) containing 1 nM of the target DNA was put on the PNA zip-code chip and placed into a hybridization chamber in which the hybridization of the target DNA with the PNA chip was performed at 37° C. for 12 hours. The target DNA has a base sequence complementary to the probe of SEQ ID NO: 7, among four PNA probes immobilized on the chip.

```
                                            (SEQ ID NO: 11)
5'-AAGAAGAAGGTCGATTACCAAAGGA-3'             (target DNA)
```

Figure 3:
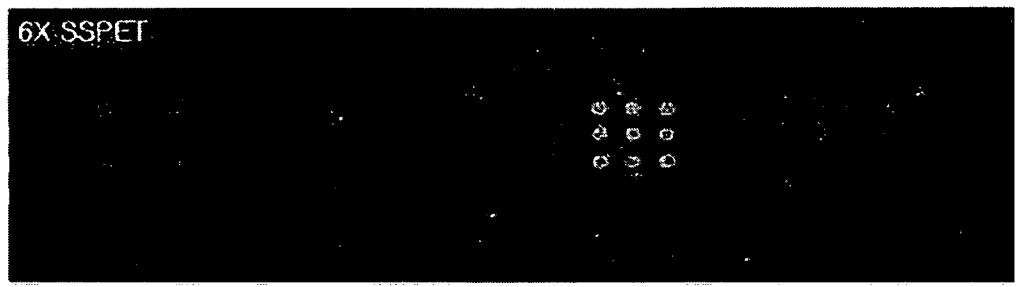
FIG. 3 shows the fluorescent image of a PNA zip-code chip hybridized with a fluorescent substance (Cy3)-labeled target DNA in 6× SSPET hybridization solution.

Thus, when hybridized with the PNA zip-code chip, a fluorescent signal must be detected in only one probe among four probes. As shown in FIG. 3, a fluorescent signal was detected only in the third PNA probe (SEQ ID NO: 7) having a complementary sequence to the target DNA, indicating that hybridization occurred only in the third probe.

Example 3

Figure 4:
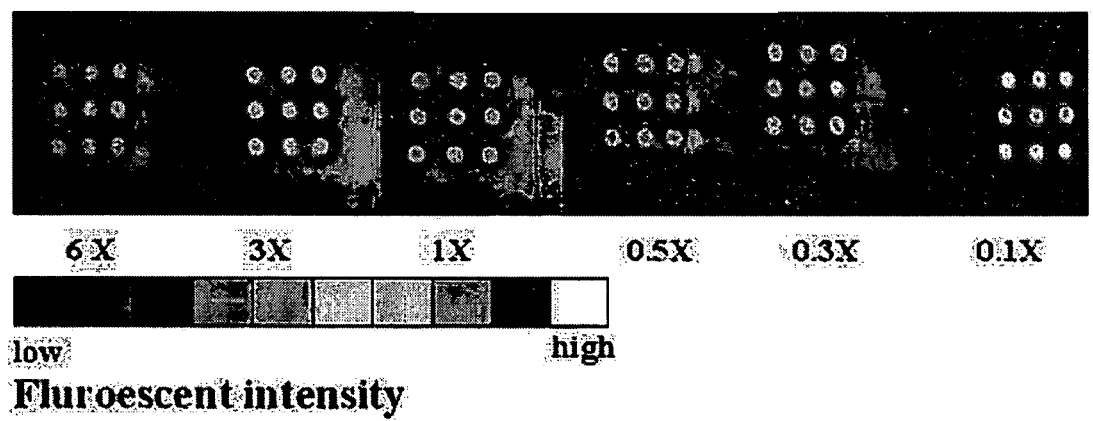
FIG. 4 shows the hybridization level according to changes in the concentration of SSPET hybridization solution.

Changes in Sensitivity of PNA Zip-Code Chip according to changes in Concentration of Hybridization Solution In order to find conditions at which the inventive PNA zip-code chip shows the most effective sensitivity, hybridizations were performed at varied concentrations of hybridization solutions. The PNA chip used in Example 2 and the target DNA (SEQ ID NO: 11) were hybridized using 0.1×, 0.3×, 0.5×, 1×, 3× and 6× SSPET hybridization solutions. As a result, the highest fluorescent signal could be observed in 0.1× SSPET hybridization solution, and the lowest fluorescent signal could be observed in 6× SSPET hybridization solution with the highest concentration (FIG. 4). It was found that the lower the concentration of hybridization solution becomes, the more effectively the hybridization of the PNA zip-code chip occurs.

Example 4

Test of the Detection Ability for Single Nucleotide Polymorphism of PNA Zip-Code Chip and DNA Zip-Code Chip In order to confirm that the ability of single nucleotide polymorphism detection of the PNA zip-code chip is superior to that of the DNA zip-code chip, the PNA and DNA probes having the same sequence were immobilized on respective aminated glass substrates, and the test results were compared.

The sequences of the probes used in the test of the ability to detect single nucleotide polymorphism are shown below, and in the case of the DNA probes, an amine group was added to the 5'-terminal end in order to link the probes with the epoxy compound upon immobilization.

```
DNA (PM)-5'-NH2-GGTAATCGACCT-3'
(DNA probe having base sequence of SEQ ID NO: 7)

DNA (MM)-5'-NH2-GGTAATTGACCT-3'
(DNA probe having single mutation sequence of
SEQ ID NO: 7)

PNA (PM)-N-GGTAATCGACCT-C
(PNA probe having base sequence of SEQ ID NO: 7)

PNA (MM)-N-GGTAATTGACCT-C
(PNA probe having single mutation base sequence of
SEQ ID NO: 7)
```

In order to examine the ability to detect single nucleotide polymorphism, hybridizations were performed using varied concentrations of hybridization solutions (0.1× SSPET, 0.3× SSPET, 1× SSPET, 3× SSPET, and 6× SSPET).

Figure 5:
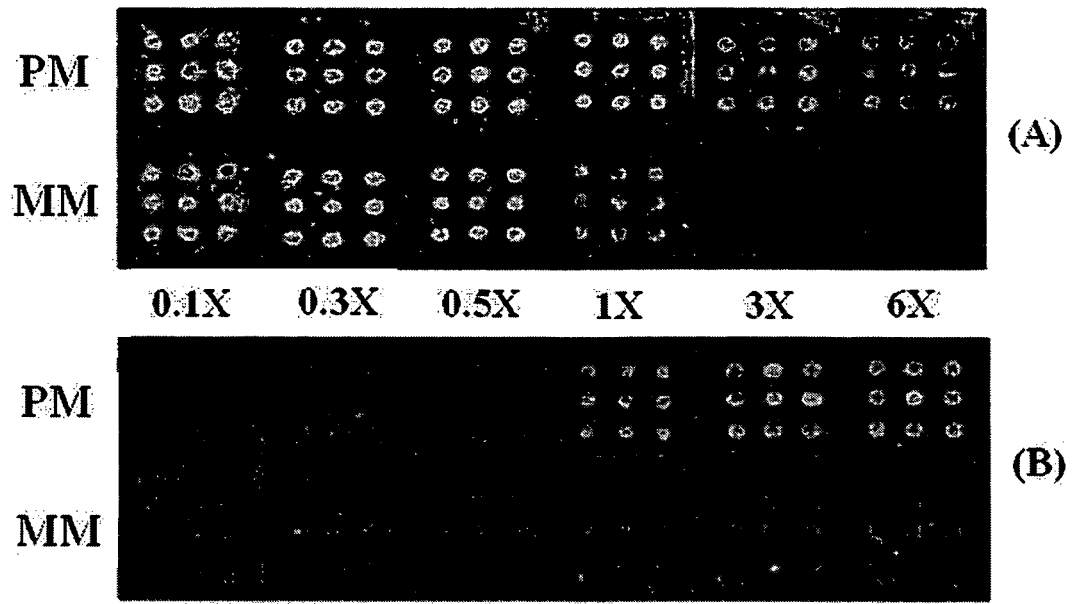
FIG. 5 shows the detection ability for single nucleotide polymorphisms of the inventive PNA zip-code chip and DNA zip-code chip according to changes in the concentration of hybridization solution.

As shown in FIG. 5, it was found that the PNA zip-code chip showed a reduction in the entire fluorescent signal value with an increase in the concentration of the hybridization solution, but the ability to detect single nucleotide polymorphism was increased. In contrast, the DNA zip-code chip showed increases in both the detection ability for single nucleotide polymorphism and the fluorescent signal value with an increase in the concentration of the hybridization solution, but the absolute value of the fluorescent signal was significantly lower than that of the PNA zip-code chip (see FIG. 5).

Example 5

Analysis of Multiple Base Mutations on PNA Zip-Code Chip (1)

In this Example, a HNF 1-α gene (SEQ ID NO: 12) associated with MODY-3, a kind of diabetes, was used as a target gene, and three base mutation sites contained in exon 2 of the gene was selected as shown in Table 1 below.

TABLE 1

| Zip code | Position | Wild-type | Mutation | Effect of Mutation |
|---|---|---|---|---|
| PNA 6P | 1845 | TCC | TTC | S142F |
| PNA 18P | 1847 | CCA | CTA | H143Y |
| PNA 31P | 1791 | TCCT | TCT | S121fsdelC |

The mutation site is bolded.

SBE primers binding to the PNA zip-code probe were designed in such manner that the 5'-terminal end had a sequence complementary to each of the PNA probes immobilized on the PNA zip-code chip and the 3'-terminal end had a sequence complementary to the target gene containing base mutations. SBE primers used in this Example were designed to have different lengths in order to maintain Tm at a uniform temperature of about 60° C. All the primers were constructed up to one base before the base mutation sites of the target gene.

For the analysis of multiple base mutations on the PNA zip-code chip, exon 2 of a HNF 1-α gene associated with diabetes was amplified by PCR. The amplified DNA was subjected to an SBE reaction using ddCTP labeled with a fluorescent substance (TAMRA). The SBE reaction was performed using three SBE primers, SBE01-6P (SEQ ID NO: 13), SBE01-18P (SEQ ID NO: 14) and SBE01-31P (SEQ ID NO: 15), in the same tube at the same time. After completion of the SBE reaction, the reaction product was hybridized with a PNA zip-code chip having 40 zip-codes immobilized thereon (Table 2).

```
                                            (SEQ ID NO: 13)
SBE01-6P:   5'-TACCAGGTCGCAGATACCACTGGCCTCAACCAG-3'

(SEQ ID NO: 14)
SBE01-18P:  5'-CGCAAGGTGCTGCACTGGCCTCAACCAGTCC-3'

(SEQ ID NO: 15)
SBE01-31P:  5'-TGCTGGGTCAGATGGTCAAGT-3'
```

TABLE 2

40 zip-codes used in Example 5

| PNA | N terminal → C terminal |
|---|---|
| 1 | TGCGGGTAATCG (SEQ ID NO: 1) |
| 2 | TGCGGGTACAGC (SEQ ID NO: 16) |
| 3 | TGCGGACCATCG (SEQ ID NO: 17) |
| 4 | TGCGGACCACCT (SEQ ID NO: 18) |
| 5 | TGCGACCTATCG (SEQ ID NO: 2) |
| 6 | TGCGACCTGGTA (SEQ ID NO: 19) |
| 7 | ATCGTGCGACCT (SEQ ID NO: 3) |
| 8 | ATCGGGTATGCG (SEQ ID NO: 4) |
| 9 | ATCGGGTAGACC (SEQ ID NO: 20) |
| 10 | ATCGGACCTGCG (SEQ ID NO: 21) |
| 11 | ATCGACCTTGCG (SEQ ID NO: 22) |
| 12 | ATCGACCTCAGC (SEQ ID NO: 23) |
| 13 | CAGCATCGTGCG (SEQ ID NO: 5) |
| 14 | CAGCATCGACCT (SEQ ID NO: 24) |
| 15 | GAGCGGTAATCG (SEQ ID NO: 25) |
| 16 | CAGCGGTAGACC (SEQ ID NO: 26) |
| 17 | CAGCGACCTGCG (SEQ ID NO: 27) |
| 18 | CAGCACCTTGCG (SEQ ID NO: 6) |
| 19 | CAGCACCTGACC (SEQ ID NO: 28) |
| 20 | GGTATGCGGACC (SEQ ID NO: 29) |
| 21 | GGTAATCGTGCG (SEQ ID NO: 30) |
| 22 | GGTAATCGACCT (SEQ ID NO: 7) |
| 23 | GGTACAGCATCG (SEQ ID NO: 31) |
| 24 | GGTACAGCGACC (SEQ ID NO: 32) |
| 25 | GGTAGACCTGCG (SEQ ID NO: 33) |
| 26 | GGTAGACCACCT (SEQ ID NO: 34) |
| 27 | GGTAACCTTGCG (SEQ ID NO: 35) |
| 28 | GGTAACCTCAGC (SEQ ID NO: 36) |
| 29 | GACTATCGTGCG (SEQ ID NO: 37) |
| 30 | GACCATCGACCT (SEQ ID NO: 8) |
| 31 | GACCCAGCATCG (SEQ ID NO: 9) |
| 32 | GACCCAGCACCT (SEQ ID NO: 38) |
| 33 | GACCACCTTGCG (SEQ ID NO: 39) |
| 34 | GACCACCTATCG (SEQ ID NO: 40) |
| 35 | ACCTATCGTGCG (SEQ ID NO: 41) |
| 36 | ACCTATCGCAGC (SEQ ID NO: 42) |
| 37 | ACCTCAGCGACC (SEQ ID NO: 43) |
| 38 | ACCTGGTAATCG (SEQ ID NO: 44) |
| 39 | ACCTGACCTGCG (SEQ ID NO: 45) |
| 40 | ACCTGACCATCG (SEQ ID NO: 10) |

Figure 6:
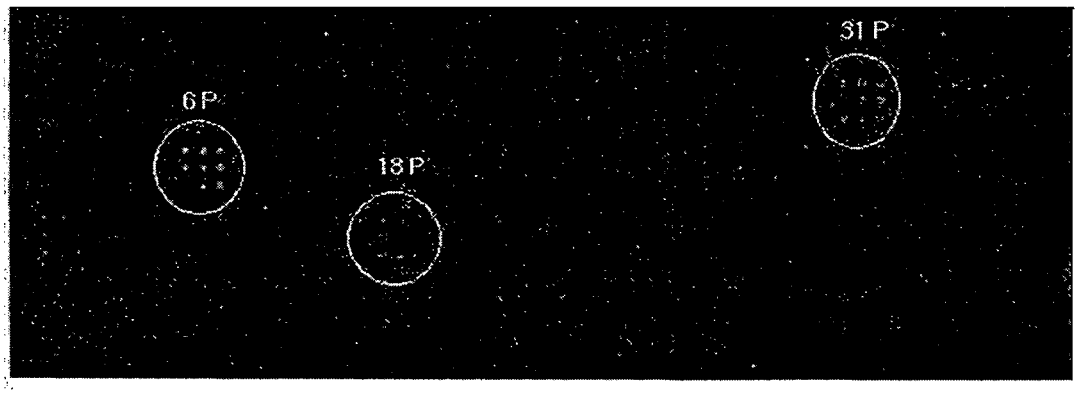
FIG. 6 shows the analysis of multiple base mutations in the PNA zip-code chip using TAMRA-ddCTP.

As a result, fluorescent signals were detected in the PNA zip-code probe 6 (SEQ ID NO: 19), the PNA zip-code probe 18 (SEQ ID NO: 6) and the PNA zip-code probe 31 (SEQ ID NO: 9) (see FIG. 6). Thus, it was found that the use of one PNA zip-code chip according to the present invention allows the analysis of multiple base mutations.

Example 6

Analysis of Multiple Base Mutations on PNA Zip-Code Chip (2)

In this Example, the target gene used in Example 5 was subjected to SBE reaction using biotin-labeled ddNTP in place of TAMRA, and the reaction product was hybridized with the chip fabricated in Example 1, which has 10 PNA zip-code probes immobilized thereon. To observe fluorescent signals, the hybridized chip was stained with phycoerythrin conjugated with streptavidin, which is a protein having strong affinity with biotin. The SBE reactions were performed using each of four reaction solutions containing biotin-dATP, biotin-dTTP, biotin-dCTP and biotin-dGTP, respectively (Table 3).

TABLE 3

Composition of reaction solution used in multiple SBE reactions

| | Set 1 | Set 2 | Set 3 | Set 4 |
|---|---|---|---|---|
| Template | 8 µl | | | |
| Primer | Addition of 10 SBE primers | | | |
| Biotin-ddNTP | Biotin-ddATP | Biotin-ddGTP | Biotin-ddCTP | Biotin-ddUTP |
| 10x reaction buffer | 2 µl | | | |
| Thermo-sequenase | 2 units | | | |
| dd H$_2$O | 3 µl | | | |

To the four reaction solutions, 10 SBE primers (SEQ ID NO: 46 to SEQ ID NO: 55) containing 10 base mutation sites were all added. The SBE primer sequences used in base mutation analysis are shown below, in which sequences complementary to the sequences of the PNA zip codes are underlined.

```
                                      (SEQ ID NO: 46)
5'-CGATTACCCGCAGCAGCACAACATCCCACAGC-3'
(SBE02-P1)

(SEQ ID NO: 47)
5'-CGATAGGTCGCATACCTGCAGCAGCACAACATC-3'
(SBE02-P2)

(SEQ ID NO: 48)
5'-AGGTCGCACGATCCGTGGCGTGTGGCG-3'
(SBE02-P3)
```

-continued

```
                                                    (SEQ ID NO: 49)
5'-CGCATACCCGATAGCAGCACAACATCCCACAG-3'
(SBE02-P4)

(SEQ ID NO: 50)
5'-CGCACGATGCTGACAGCGGGAGGTGGTCG-3'
(SBE02-P5)

(SEQ ID NO: 51)
5'-CGCAAGGTGCTGCACTGGCCTCAACCAGTCC-3'
(SBE02-P6)

(SEQ ID NO: 52)
5'-AGGTCGATTACCGACGCAGAAGCGGGCC-3'
(SBE02-P7)

(SEQ ID NO: 53)
5'-AGGTCGATGGTCAACCAGTCCCACCTGTCCCAAC-3'
(SBE02-P8)

(SEQ ID NO: 54)
5'-CGATGCTGGGTCTCCCATGAAGACGCAGAAGC-3'
(SBE02-P9)

(SEQ ID NO: 46)
5'-CGATGGTCAGGTCCTACCTGCAGCAGCACAACA-3'
(SBE02-P10)
```

After completion of the SBE reactions, each reaction product was hybridized with the PNA zip-code chip.

Figure 7:
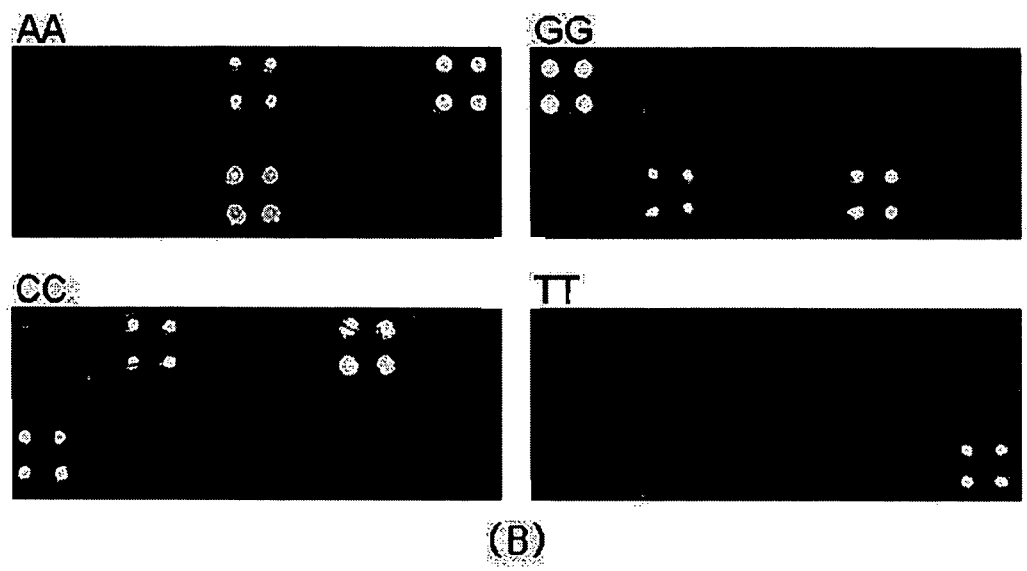
FIG. 7 shows fluorescent images obtained by performing the simultaneous analysis of several base mutation sites in a PNA zip-code chip fabricated according to one embodiment of the present invention.
Figure 8:
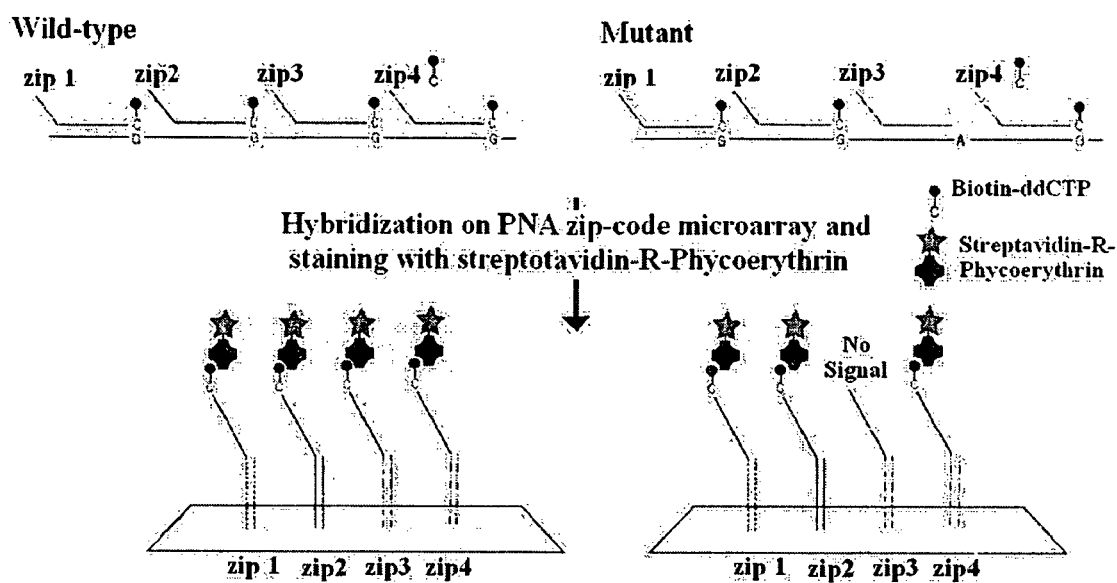
FIG. 8 schematically depicts a method for analyzing base mutations using the PNA zip-codes according to Example 6 of the present invention.

FIG. 7 shows the results of observation by a fluorescent scanner on the PNA zip-code chips which have been hybridized with the product from the SBE reaction conducted at each set and then stained with streptavidin-conjugated phycoerytbrin. As shown in FIG. 7(B), the chip expected to show an AA phenotype (introduced with biotin-ddATP) showed a fluorescent signal only at the AA phenotype. The remaining three cases (GG, CC and TT) also showed precisely the same results as expected. This suggests that 10 base mutation sites can be precisely diagnosed by one SBE reaction within one tube. The use of this method allows base mutation sites or SNPs associated with several diseases to be analyzed in large numbers at the same time. FIG. 8 schematically shows the method for analyzing base mutations according to Example 6.

As described above, the present invention provides a method for fabricating a PNA zip-code chip using zip-codes, which comprises linking the PNA probe to the aminated substrate using the epoxy compound as a linker. Also, the present invention provides a PNA zip-code chip fabricated by this method, in which the substrate and the PNA zip-code probe are linked with each other using the epoxy compound as a linker. In addition, the present invention provides methods to detect DNA and to analyze multiple base mutations and SNPs, which comprise using the PNA chip.

According to the present invention, the use of PNA, having more excellent properties than those of DNA, allows precise diagnosis of congenital diseases or base mutations with much higher sensitivity than is achievable with the DNA chip. Additionally, the use of the PNA zip-code chip makes it possible to diagnose gene mutations in a simple manner, only by hybridization reaction, without troublesome processes in which probes must be immobilized directly on a substrate every time target gene changes.

Although the present invention has been described in detail with reference to the specific features, it will be apparent to those skilled in the art that this description is of an illustrative character only, and is not to be construed limitingly, as regards the scope of the present invention. Thus, the substantial scope of the present invention will be defined by the appended claims and equivalents thereof. Those skilled in the art will appreciate that simple modifications, variations and additions to the present invention are possible, without departing from the scope and spirit of the invention as disclosed in the accompanying claims.

What is claimed is:

1. A method of fabricating a PNA chip using zip-codes, the method comprising the steps of:

(a) spotting a mixture of dimethylsulfoxide (DMSO), a plurality of PNA probes comprising zip-code sequences having a homology of less than 30% with each other and an epoxy compound represented by the following formula 1, on an aminated substrate so as to immobilize the PNA probes on the substrate; and (b) washing the PNA probe-immobilized substrate with an SDS solution, followed by drying:

[Formula 1]

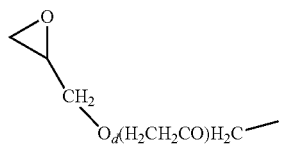

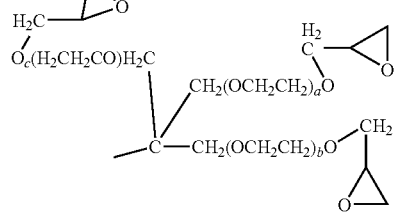

where: $a + b + c + d \sim 3$.

2. The method according to claim 1, wherein the volume ratio of the dimethylsulfoxide (DMSO), the PNA probes wherein the concentration of the PNA probes is in a range of from 10 μM to 1 mM and the epoxy compound in the step (a) is 1:1:1.

3. The method according to claim 1, wherein each PNA probe comprises any one of SEQ ID NO: 1 to SEQ ID NO: 10.

* * * * *

UNITED STATES PATENT AND TRADEMARK OFFICE
CERTIFICATE OF CORRECTION

PATENT NO. : 7,659,064 B2
APPLICATION NO. : 11/113534
DATED : February 9, 2010
INVENTOR(S) : Hyun-Gyu Park Page 1 of 1

It is certified that error appears in the above-identified patent and that said Letters Patent is hereby corrected as shown below:

Title Page; item (73); Page 1, column 1, Assignee information, "Korea Advanced Institute of Sciences and Technology" should be -- Korea Advanced Institute of Science and Technology --.

Column 2, line 7, "flame" should be -- frame --.

Column 2, lines 39-40, "antinated" should be -- aminated --.

Column 4, line 21, "HNF 1-á" should be -- HNF 1-a --.

Column 4, line 56, "phycoerytlrin" should be -- phycoerythrin --.

Column 5, line 8, "zipcode" should be -- zip-code --.

Column 5, line 36, "zipcode" should be -- zip-code --.

Column 8, line 23, "HNF 1-á" should be -- HNF 1-a --.

Column 8, line 38, "5'-terninal" should be -- 5'-terminal --.

Column 8, line 48, "HNF 1-á" should be -- HNF 1-a --.

Column 11, lines 31-32, "phycoerytbrin" should be -- phycoerythrin --.

Column 36, line 12 (claim 1), "where" should be -- wherein --.

Signed and Sealed this

Tenth Day of August, 2010

David J. Kappos
*Director of the United States Patent and Trademark Office*